(12) United States Patent
Kanagaratnam et al.

(10) Patent No.: US 11,547,342 B2
(45) Date of Patent: Jan. 10, 2023

(54) METHOD AND APPARATUS FOR ANALYSING CHANGES IN THE ELECTRICAL ACTIVITY OF A PATIENT'S HEART IN DIFFERENT STATES

(71) Applicant: IMPERIAL COLLEGE INNOVATIONS LIMITED, London (GB)

(72) Inventors: Prapa Kanagaratnam, London (GB); Darrel Parthipan Francis, London (GB); Matthew Shun-Shin, London (GB)

(73) Assignee: IMPERIAL COLLEGE INNOVATIONS LTD, London (GB)

( * ) Notice: Subject to any disclaimer, the term of this patent is extended or adjusted under 35 U.S.C. 154(b) by 0 days.

(21) Appl. No.: 15/781,097

(22) PCT Filed: Dec. 2, 2016

(86) PCT No.: PCT/EP2016/079567
§ 371 (c)(1),
(2) Date: Jun. 1, 2018

(87) PCT Pub. No.: WO2017/093474
PCT Pub. Date: Jun. 8, 2017

(65) Prior Publication Data
US 2018/0353097 A1 Dec. 13, 2018

(30) Foreign Application Priority Data
Dec. 4, 2015 (GB) ...................................... 1521477

(51) Int. Cl.
*A61B 5/00* (2006.01)
*A61B 5/35* (2021.01)
(Continued)

(52) U.S. Cl.
CPC ................ *A61B 5/35* (2021.01); *A61B 5/339* (2021.01); *A61B 5/4884* (2013.01); *A61B 5/7246* (2013.01); *G16Z 99/00* (2019.02)

(58) Field of Classification Search
CPC .................................................. A61B 5/04525
See application file for complete search history.

(56) References Cited

U.S. PATENT DOCUMENTS 4,649,924 A 3/1987 Taccardi
5,419,337 A 5/1995 Dempsey et al.
(Continued)

FOREIGN PATENT DOCUMENTS

WO 2012/092016 A1 7/2012
WO 2013/152066 A1 10/2013

OTHER PUBLICATIONS

Combined Search and Examination Report issued for Application No. GB1521477.8 dated May 24, 2016.
(Continued)

*Primary Examiner* — John R Downey
*Assistant Examiner* — Anant A Gu Pta
(74) *Attorney, Agent, or Firm* — Kilpatrick Townsend & Stockton LLP (57) ABSTRACT

A method of analysing changes in the electrical activity of a patient's heart between a reference state and a test state, the method using a reference data set of electrophysiological data captured from the patient in the reference state and at least one test data set of electrophysiological data captured from the patient in the test state, each data set defining a plurality of electrograms for a respective plurality of spatial locations relative to the heart, the method comprising processing the electrophysiological data by, matching each electrogram in the reference data set to a corresponding electrogram in the at least one test data set to create a pair
(Continued)

of electrograms for each of the plurality of spatial locations, and deriving a time delay for each spatial location by calculating the time delay between the electrograms of the pair of matched electrograms for that spatial location.

20 Claims, 4 Drawing Sheets

(51) Int. Cl.
*A61B 5/339* (2021.01)
*G16Z 99/00* (2019.01)

(56) References Cited

U.S. PATENT DOCUMENTS

| | | | |
|---|---|---|---|
| 5,431,691 A | 7/1995 | Snell et al. | |
| 6,236,883 B1* | 5/2001 | Ciaccio | A61B 5/363 600/515 |
| 6,308,093 B1 | 10/2001 | Armoundas et al. | |
| 7,123,954 B2* | 10/2006 | Narayan | A61B 5/04525 600/518 |
| 7,983,743 B2 | 7/2011 | Rudy et al. | |
| 9,662,178 B2* | 5/2017 | Nanthakumar | A61B 5/0422 |
| 2001/0039443 A1 | 11/2001 | Chen | |
| 2004/0039292 A1 | 2/2004 | Schlegel et al. | |
| 2004/0073262 A1* | 4/2004 | Lovett | A61N 1/3622 607/5 |
| 2004/0122332 A1* | 6/2004 | Macadam | A61B 5/7445 600/515 |
| 2007/0191901 A1* | 8/2007 | Schecter | A61B 5/0538 607/17 |
| 2008/0188765 A1* | 8/2008 | Stolarski | A61B 5/062 600/518 |
| 2009/0053102 A2 | 2/2009 | Rudy et al. | |
| 2009/0227884 A1* | 9/2009 | Saumarez | A61N 1/37 600/523 |
| 2009/0299211 A1* | 12/2009 | Wenzel | A61B 5/0215 600/547 |
| 2012/0123283 A1 | 5/2012 | Tikkanen et al. | |
| 2012/0184858 A1* | 7/2012 | Harlev | A61B 5/0402 600/484 |
| 2013/0245473 A1* | 9/2013 | Ramanathan | A61B 5/318 600/509 |
| 2014/0148677 A1 | 5/2014 | Liempde et al. | |
| 2014/0235989 A1* | 8/2014 | Wodlinger | A61B 5/066 600/374 |
| 2015/0201859 A1 | 7/2015 | Baker et al. | |
| 2015/0216438 A1* | 8/2015 | Bokan | A61B 5/316 600/515 |

OTHER PUBLICATIONS

Elias Ebrahimzadeh et al., "A Novel Approach to Predict Sudden Cardiac Death (SCD) Using Nonlinear and Time-Frequency Analyses from HRV Signals", PLOS ONE, vol. 9, Issue 2, Feb. 2014, e81896, pp. 1-14.

Gabriela Hilfiker et al., "Utility of electrophysiological studies to predict arrhythmic events", World Journal of Cardiology, Jun. 26, 2015, 7(6), pp. 344-350.

International Search Report and Written Opinion issued in Application No. PCT/EP2016/079567 dated Feb. 20, 2017.

Jiapu Pan et al., "A Real-Time QRS Detection Algorithm", IEEE Transactions on Biomedical Engineering, vol. BME-32, No. 3, Mar. 1985, pp. 230-236.

Ramin Shadman et al., "A novel method to predict the proportional risk of sudden cardiac death in heart failure: Derivation of the Seattle Proportional Risk Model", Heart Rhythm, vol. 12, No. 10, Oct. 2015, pp. 2069-2077.

Matthew J Shun-Shin et al., "Rapid Identification of an Arrhythmogenic Substrate in Sudden Cardiac Death Survivors Using Relative Activation Mapping to Show Failure of Rate Adaptation", J. Interv. Card Electrophysiol, 2016, 45, pp. 297-298.

European Patent No. EP16805140.7, "Office Action", dated Jan. 31, 2020, 5 pages.

* cited by examiner

METHOD AND APPARATUS FOR ANALYSING CHANGES IN THE ELECTRICAL ACTIVITY OF A PATIENT'S HEART IN DIFFERENT STATES

CROSS-REFERENCE TO RELATED APPLICATIONS

This application is a U.S. National Stage of PCT Application No. PCT/EP2016/079567, filed Dec. 2, 2016, which claims priority to Foreign Application No. 1521477.8 GB, filed Dec. 4, 2015. Each of these applications is hereby incorporated by reference in its entirety for all purposes.

TECHNICAL FIELD

This invention relates generally to the field of heart rhythm disorders and more specifically to systems and methods for analysing electrograms and mapping of the heart under various stimuli for the diagnosis, treatment, and risk-stratification of cardiac conditions.

BACKGROUND

Although it is now possible to collect large amounts of electrical information about the electrical changes that occur in the heart throughout the cardiac cycle, it is still difficult to process this information to predict which patients are prone to abnormalities of electrical behaviour including arrhythmias and sudden death.

Tests are available to stimulate the heart for example with pharmacological agents (for example, ajmaline, adrenaline, isoprenaline, and flecainide) or physiological stimuli (for example, exercise or change of body position on a tilt-table). Moreover, there is also a variety of ways of acquiring electrical information on the heart, including from electrograms obtained from electrodes placed on the body surface, from electrodes placed within the heart, or from electrodes placed on the surface of the heart, or any combination of these. Furthermore, this electrical information can be processed to derive electrograms that describe an imputed electrical state on the surface of the heart.

The current state-of-the-art of interpretation of these electrical data involves a human expert inspecting the data, often displayed graphically, to detect patterns or make measurements. A common challenge is the reliable identification of the time of an electrical event at an electrode, because the electrical signal is a curve, whose interpretation may vary between experts. Moreover, comparison of signals from adjacent points on the electrical signal curve may differ so that there is even more uncertainty for the expert as to which instant on a second curve corresponds to the identical point on the first curve.

The weaknesses of the current state of the art include:

a) Expertise in interpretation is relatively scarce.
b) The time taken to manually annotate times of electrical events means that even if large amounts of data are collected, only a small proportion can be analysed in a practical timeframe.
c) It is difficult to describe and visually present, in terms of quantity and spatial localisation, the patterns of degree of change of electrical events under different conditions.
d) There can be multiple conflicting interpretations of the same data.

US2012123283 describes an approach to predicting the risk of sudden cardiac death based on analysis of electrocardiograms. US2014148677 describes an approach to providing an electrical activity map of the heart using signals acquired by a plurality of surface electrodes. US2004039292 describes a system for the diagnosis and monitoring of coronary artery disease, acute coronary syndromes, cardiomyopathy and other cardiac conditions. U.S. Pat. No. 7,983,743 describes non-invasive systems and methods for determining electrical activity for a heart of a living being.

SUMMARY OF THE INVENTION

It is a general aim of embodiments of the present invention to provide improved methods for analysing electrical data from the heart, for example to predict a patient's susceptibility to abnormalities of electrical behaviour including arrhythmias and sudden death. Embodiments of the invention are particularly suited to analysing large volumes of data, for example from data from 100 or more electrodes and/or 500 or more electrograms at a given point in time, to quickly provide a useful output for a medical practitioner.

The general approach adopted by embodiments of the invention is to look at changes in the timing of electrical signals from the heart, for a plurality of locations on the heart, between a rest (or other reference) state and a stimulated (or other test) state. For a given spatial location on the heart one or more electrograms acquired from the patient in the rest state are compared with one or more electrograms acquired from the patient in the stimulated state, this being repeated for multiple locations.

Consequently, the comparison is between electrograms for the same location on the heart under different conditions. This contrasts with earlier approaches to analysing electrical data from the heart, which have sought to match electrograms at different locations on the heart to track an electrical signal moving across the heart. Taking the approach proposed for the present invention, matching electrograms becomes more straightforward as the shape of the electrical signal for a given location is generally the same or very similar under the different states, whereas the shape of the signal can change significantly as it travels across the heart, making matching the electrograms very difficult. This in turn leads to simpler and therefore quicker analysis when adopting the approach proposed for the present invention, meaning automation of the analysis becomes more straightforward.

The term "electrogram" as used herein refers to a sequence of data representing changes over time in an electrical signal at a particular spatial location. Typically a single electrogram will be a record of the electrical signal for a single beat of the heart. Whilst it is possible to display an electrogram graphically the term "electrogram" as used herein is not limited to a graphical representation of the data and also includes, for example, the data stored in computer memory.

In a first aspect, the invention provides a method of analysing changes in the electrical activity of a patient's heart between a reference state and a test state, the method using a reference data set of electrophysiological data captured from the patient in the reference state and at least one test data set of electrophysiological data captured from the patient in the test state, each data set defining a plurality of electrograms for a respective plurality of spatial locations relative to the heart;

the method comprising processing the electrophysiological data by:

matching each electrogram in the reference data set to a corresponding electrogram in the at least one test data set to create a pair of electrograms for each of the plurality of spatial locations; and deriving a time delay for each spatial location by calculating the time delay between the electrograms of the pair of matched electrograms for that spatial location.

In a second aspect, the invention provides an apparatus for analysing changes in the electrical activity of a patient's heart between a reference state and a test state, the apparatus comprising:

a memory storing a reference data set of electrophysiological data captured from the patient in the reference state and at least one test data set of electrophysiological data captured from the patient in the test state, each data set defining a plurality of electrograms for a respective plurality of spatial locations relative to the heart; and a processor that can access data in the memory and is operable to:

match each electrogram in the reference data set to a corresponding electrogram in the at least one test data set to create a pair of electrograms for each of the plurality of spatial locations; and a time delay for each spatial location by calculating the time delay between the electrograms of the pair of matched electrograms for that spatial location.

In some embodiments, the reference state is a rest state and the test state is a post-stimuli state following application of a physiological or pharmacological stimulus to the patient. The physiological stimulus may, for example, be exercise or change of body position. Exemplary pharmacological stimulus include ajmaline, adrenaline, isoprenaline, and flecainide. Alternatively, the reference state could be a stress state (e.g. following stimulus) and the test state could be a rest state. In fact, in embodiments of the invention, multiple physiological data sets could be acquired from a patient over time and in different states and the approach described and claimed herein can be used to compare any two or more of the data sets. It is possible, for example, to analyse a sequence (e.g. time sequence) of data sets, each data set being compared with the preceding data set in the sequence.

In some embodiments, the spatial locations are locations on the internal or external surface of the heart.

In some embodiments, the method further comprises generating an output that comprises the spatial locations and associated time delays. The output may be displayed to a user (e.g. a medical practitioner).

In some embodiments, displaying the output to a user comprises representing the spatial locations in a two-dimensional map and indicating relative magnitudes of the time delays associated with the spatial locations at the respective position on the two-dimensional map. The relative magnitudes may be actual time delays. More preferably they represent time delay differences ("deltas") for each location with respect to a reference time delay, for example with respect to an average (e.g. mean or median) of all the time delays for all spatial locations encompassed by the output. The relative magnitudes may be specific values for each point on the map. Alternatively, the relative magnitudes may be bands of values, so rather than each point on the map displaying a specific value it instead displays that respective band within which the time delay or "delta" for that spatial location falls. The representation of the relative magnitudes on the map may also indicate a "direction" of the difference; that is whether the "delta" for a given location is negative or positive (i.e. whether the time delay at that point is more or less than the reference time delay). Where the relative magnitudes are displayed in bands, the boundaries between bands may be considered as thresholds. In a simple case, there may be just a single threshold, with all time delays or "deltas" below the threshold being in one band and those above the threshold in another. In other examples, there may be two or more thresholds to either side of the reference time delay.

The relative magnitudes (e.g. bands and direction) of the time delays may be indicated by different colours and/or intensity of colour.

In some embodiments the location of one or more cardiac structures can also be indicated on the two-dimensional map.

In some embodiments, the method comprises generating an output that represents a summary of the time delays over the whole heart (or a specific region of interest comprising multiple spatial locations). The summary output may, for example, be a function of all of the relative magnitudes (e.g. a function of the "deltas" for all relevant spatial locations). For instance, the summary output may be a standard deviation of all of the "deltas".

In some embodiments the output (e.g. the 2D map or the summary output) may be compared with a control output to provide a measure of the susceptibility of the patient's heart to developing arrhythmias. For example, the 2D map may be compared with a 2D map for a healthy heart and/or one or more 2D maps for hearts that are susceptible to abnormal electrical behaviour, such as arrhythmias or sudden cardiac death. The comparison could be with the same patient's data from a previous investigation, for example to assess changes in the condition of the heart, or with data from exemplar patients or from "model" data (e.g. average data from multiple patients).

In another example, the summary output (e.g. standard deviation of "deltas") could be compared with one or more threshold values to give a measure of the susceptibility (e.g. "no risk", "low risk", "medium risk" or "high risk").

In some embodiments, the method comprises a data acquisition step prior to processing of the electrophysiological data, the data acquisition step comprising acquiring the reference set of electrophysiological data from the patient, changing a state of the patient, and then acquiring the at least one test set of electrophysiological data from the patient. Changing the state of the patient may comprises applying a physiological or pharmacological stimulus to the patient, as discussed above.

In some embodiments, once the data has been acquired, there may be a data pre-processing step to "clean" the electrophysiological data, comprising, for example filtering the acquired data, smoothing the acquired data and/or transforming the acquired data.

In some embodiments, each electrogram is directly measured by an electrode, the spatial locations being the locations of the electrodes, and the step of matching an electrogram in the reference data set to a corresponding electrogram in the at least one test data set comprises matching electrograms measured by the same electrode.

Alternatively, in some embodiments it may be desirable to infer electrograms on e.g. the heart surface from signals from electrodes on the patient's skin. In this case, the spatial locations are locations on the heart's surface (inferred from the electrode signals). In this case, as with the case above, the step of matching an electrogram in the reference data set to a corresponding electrogram in the at least one test data set may comprise matching electrograms calculated using signals from the same electrode or electrodes. However, where electrograms on the heart are being inferred from electrodes on the patient's skin, the position of the electrodes relative to the heart can shift and this can lead to a mis-match of electrograms when they are compared.

In some embodiments, therefore, the step of matching an electrogram in the reference data set to a corresponding electrogram in the at least one test data set comprises calculating a degree of similarity between the electrogram from the reference data set and each of a plurality of electrograms from the test data set, the electrogram from the test data set with the highest degree of similarity being selected as the corresponding electrogram to match to the electrogram from the reference data set.

To improve the accuracy of the matching, for each of said plurality of electrograms from the test data set a degree of similarity may be calculated for each of a plurality of different assumed time delays.

Whilst, for each electrogram in the reference data set, a degree of similarity could be calculated for every electrogram in the test data set, this would be very processor intensive and also runs a risk of false matches of points that are spaced far apart. Thus, in some embodiments, for each electrogram in the reference data set a degree of similarity is calculated only for a subset of the electrograms in the test data set. The subset of electrograms in the test data set may be selected based on their spatial proximity to the electrogram in the reference data set with respect to which the degree of similarity is being calculated.

In some embodiments, the electrophysiological data captured from the patient using electrodes is captured with associated spatial data defining the location of the electrodes relative to one another and/or relative to anatomical landmarks. This associated spatial data can be used to determine the spatial proximity of electrograms.

In some embodiments, calculating the time delay between the electrograms comprises dividing each electrogram into two or more segments and calculating the time delay between one or more corresponding segments of the matched electrograms. For example, it may be decided to compare only the QRS complex components of the electrograms, or just the T-wave, or just the P-wave components.

In some embodiments, the electrophysiological data comprises multiple electrograms for each spatial location, the time delay being derived by matching multiple electrograms in the reference data set to a corresponding number of electrograms in the at least one test data set to create multiple pairs of electrograms for each of the plurality of spatial locations from which the time delay can then be derived. The multiple electrograms may, for example, represent multiple heart beats (each electrogram representing one beat). The multiple electrograms may be multiple consecutive electrograms together representing a complete respiratory cycle.

Where multiple electrograms are acquired for each spatial location then for each spatial location the time delays between the multiple matched pairs of electrograms can be averaged to determine the time delay for that spatial location. Alternatively, each electrogram in a set of electrophysiological data that is to be matched with its pair can itself be an average of multiple electrograms for the respective spatial location.

By averaging out multiple electrograms for each location, or the time differences between multiple matched pairs of electrograms for each location, discrepancies in the data (e.g. due to noise or cyclical variations in the electrical signals) become less influential.

DETAILED DESCRIPTION

The invention will now be further described with reference to the following non-limiting Figures and Examples. Other embodiments of the invention will occur to those skilled in the art in the light of these.

The invention is exemplified with reference to methods for generating a model of the dynamic change of a plurality of electrograms recorded from or about the heart when subject to internal and external stimuli. Measured or calculated electrograms associated with spatial localisation data are matched between two time-points and indices of time-delay are calculated based on maximising the similarity for each pair of electrograms. The 3-dimensional spatial data is then transformed into pairs of angular co-ordinates (elevation and azimuth) in relation to orthogonal axes. These pairs of angular co-ordinates are then transformed (projected) and graphically displayed using a marker representing the scalar value of the time-delay to generate a map of the spatial heterogeneity in changes of time-lag of cardiac electrical data between a reference and post-stimuli test time-point.

Embodiments of the invention are useful in medical practice in assessing the electrical changes of the heart to stimuli. Applications of this include assessing the risk of developing arrhythmias. One example is identifying patients at high risk of future sudden arrhythmias including fatal arrhythmia (sudden death). Another example is assessing the response of an individual patient to one or more drugs. The intention might be to identify the drug that has the greatest or least effect. For example, some drugs increase risk of arrhythmias in some patients, and for these drugs assessing subtle drug induced changes in electrical patterns can be desirable. In some situations, where there is high concern for potential arrhythmogenicity, for example in athletes or participants in highly competitive sport, embodiments of this invention can be useful for their assessment.

Embodiments of the invention are typically implemented in software running on a general purpose computer or computer network, although specialist computing devices may also be used in some cases.

Figure 1:
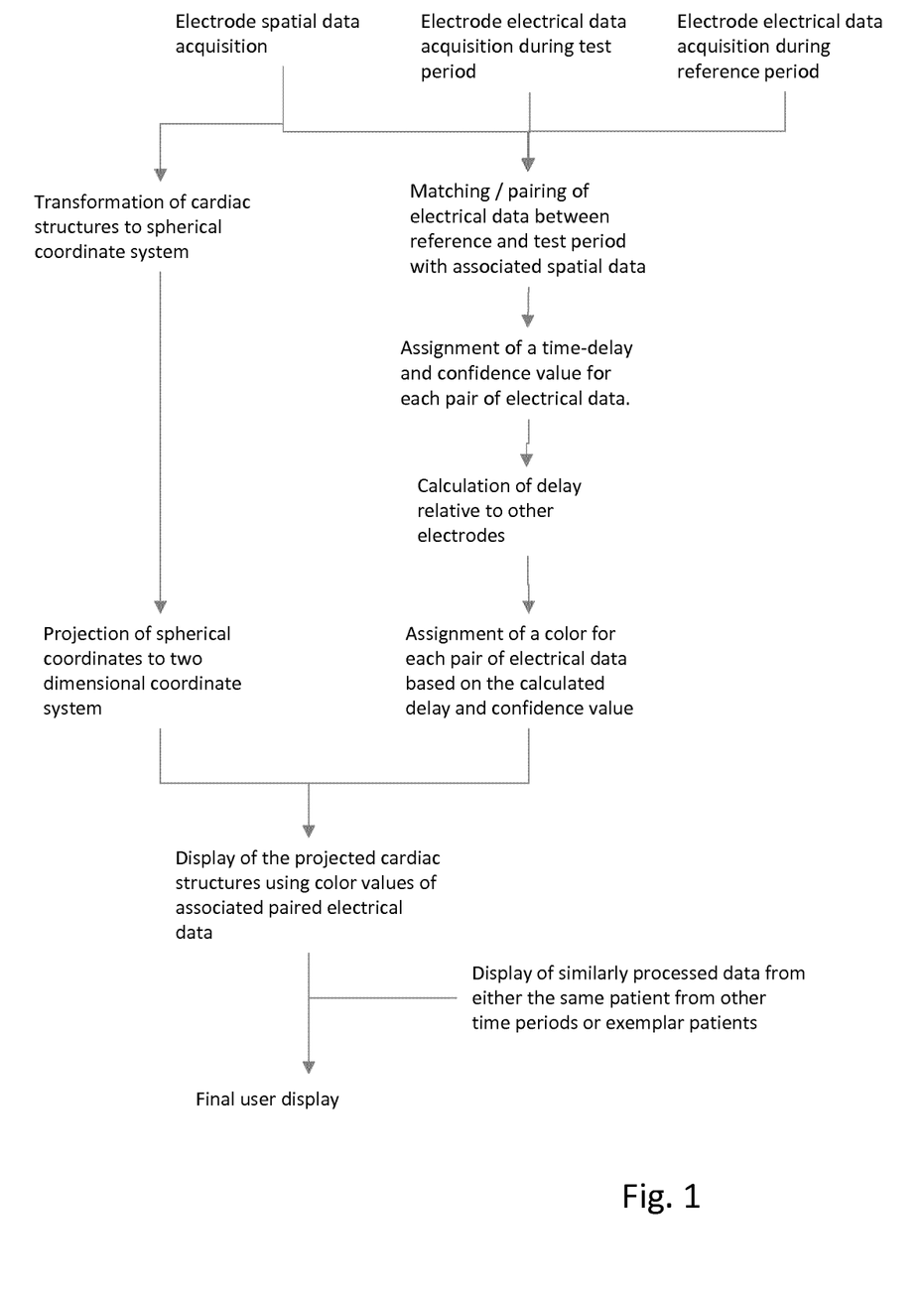
FIG. 1 sets out a flow diagram for a method of analysing electrical heart data in accordance with an embodiment of the present invention.

FIG. 1 illustrates an exemplary method in accordance with an embodiment of the invention. The method can be broken down into four main phases:

a) Acquiring electrical data (before and after stimulus), along with spatial data;
b) Applying a stimulus that changes the state of the heart;
c) Processing the acquired electrical and spatial data; and
d) Displaying the output of the processing phase to an operator.

Each of these phases will be discussed in more detail in turn below.

Acquiring Electrical Data

A variety of methods for obtaining electrograms are well known to those skilled in the art. The most invasive method is to place multiple electrodes on the internal or external surfaces of the heart. In an alternative embodiment, the signals are obtained non-invasively by electrodes contacting the skin of the surface of the body.

Advantageously, this can be a large array of electrodes that can be placed on the surface of the body to acquire a large number of signals simultaneously (e.g. such as available from Cardioinsight Technologies Inc, Medtronic, USA; Amycard, EP Solutions, Switzerland). A further advantage can be gained by these signals being processed to derive estimates of what the electrical signal would be had it been acquired directly from the internal or external surface of the heart. An example of such a processing method is described in US 20090053102.

Stimuli

The electrical substrate of the heart is labile in the presence of intrinsic and extrinsic stimuli or stressors such as physiological stimuli (including exercise and change in posture), and pharmacological stimuli (including ajmaline, adrenaline, isoprenaline, and flecanide). Electrode data can be obtained in the reference state, for example, at rest and recumbent, or semi-recumbent, or standing, and during or after the intervening test where the stimulus is performed, e.g. exercise, on stopping exercise, after the administration of a pharmacological agent, or a change in posture. Advantageously, data can be collected throughout the period of the stimulus allowing comparison at multiple time-points.

Processing

The electrical data begins as a set of electrical graphs (or data that could be represented as graphs) over time, each of which represents a function of voltage at a different position. This data is referred to generally herein as electrograms. The spatial data that is captured also includes the locations of cardiac structures.

As shown in FIG. 1, the data representing the cardiac structures is transformed to a spherical coordinate system and then projected to a two dimensional coordinate system (in the manner discussed below for the electrical heart data) for display, alongside the electrical heart data.

The electrical heart data that has been acquired first goes through a matching process to match electrograms in the reference data set to corresponding electrograms in the test data set. Each matched pair of electrograms is stored along with related spatial data (e.g. indicating the location on the heart that the electrogram pair is associated with).

For each matched pair of electrograms, a time delay is then calculated between the reference electrogram and the test electrogram. This is recorded along with a confidence value for each pair. Once the time delay has been calculated for all pairs, a relative delay for each pair is then calculated (e.g. relative to an average for all pairs).

For generating a display of the relative delay, a colour is assigned to each matched pair based on the calculated relative delay and the confidence value.

The projected two dimensional cardiac structures are then displayed on a 2D map along with the colour values representing the relative delay for each pair of electrograms in their respective positions relative to the cardiac structures. In some cases this map is displayed along with (e.g. alongside) similarly processed control data, e.g. for the same patient from a previous time period or for an exemplar patient, to provide a final display for the user.

These processing steps are now described in more detail.

Electrogram Pre-Processing

In step 1 a reference cardiac cycle template (i.e. a reference electrogram for each of a plurality of spatial locations) is created. In a simple embodiment, this is done by identifying a single heart beat within the electrical data. In an alternative embodiment this is done by identifying a set of several beats, segmenting them into individual beats, aligning them at a time of a maximal index of similarity (for example, maximal correlation, minimal Manhattan distance, or any other technique known to those skilled in the art), and then averaging the overlying signals. The advantage of this is that the effect of small cyclical fluctuations in electrical signal over time is reduced. Conveniently the period of the averaging is at least one respiratory cycle.

Any one of many available algorithms may be used for this process of constructing the reference cardiac cycle template from a set of beats. An example is detailed below.

a) Detect the peak, or maximal rate of deflection of the QRS complex on the electrograms [Pan, Tompkins; IEEE Transactions on Biomedical Engineering, Vol BME-32, No 3, p 230-255].

b) Divide the interval of time between the R wave events so that the first part of the interval is considered belonging in the previous cycle, and the second part considered to belongs to the next cycle.

c) By this process, for each cycle, a contiguous period of time is obtained, consisting of some part before the start of the R wave, and some part after the R wave. These data for each cycle are therefore aligned by the time marked as the start of the R wave.

d) The series of cycles described in step c is then averaged across the cycles to produce a single template cycle.

A variety of methods can be applied to handle small variations in duration of each cycle. For example, the averaging could be restricted to the duration of the shortest cycle. Alternatively, the data could be interpolated to extend the number of data-points, or alternatively down-sampled to reduce the number of data-points to achieve the same number of data-points per cycle.

In step 2 the patient receives the stimulus (for example exercise), and the process described in step 1 in repeated in the test state.

Advantageously, in optional step 3, the electrogram data can be pre-processed to remove noise, artefacts, and optimise matching. For example, noise may be removed with high-pass, low-pass, or band-pass filters to remove movement artefact, mains electrical noise, or other sources of noise known to those skilled in the art. The electrogram may be smoothed using one of the many algorithms known to those skilled in the art, for example using a Savitzky-Golay filter. The electrogram signals can optionally be transformed before the matching and time-delay calculation. Any one of many transformations may be applied before the subsequent processing steps, e.g.

a) No transformation
b) Log transformation
c) Rectification using the absolution or square of the signal.
d) Calculation of the first derivative.
e) Calculation of the negative first derivative.
f) Calculation of the negative first derivative with negative values of the derivative set to a constant (for example 0).

Electrogram Matching

In the next stage for each point a time delay is derived between the signal acquired on the electrode in the test state and the signal acquired from the corresponding electrode in the reference state. At this point it should be borne in mind that an electrode may have one position in reference to the heart in the reference state, but may have a different position in reference to the heart in the test state. For example, during exercise or tilt testing, the upper body movements can easily cause skin and underlying tissues to move significantly with respect to the heart. It is therefore advantageous for the process, which accounts for this, that no assumption is made that the electrode in the test state is most closely equivalent in space to the same electrode in the reference state. For this reason additional steps are provided as below to match electrograms in the reference and test data sets to one another.

In step 4 the appropriate corresponding electrode in the reference state is identified for each electrode in the test state. In the simplest embodiment, the assumption is made that the position of the electrodes do not significantly change, and therefore the corresponding electrode in the resting state is simply the same electrode. In an advantageous embodiment a series of steps are performed to determine the most suitable corresponding electrode, as described below.

Figure 2:
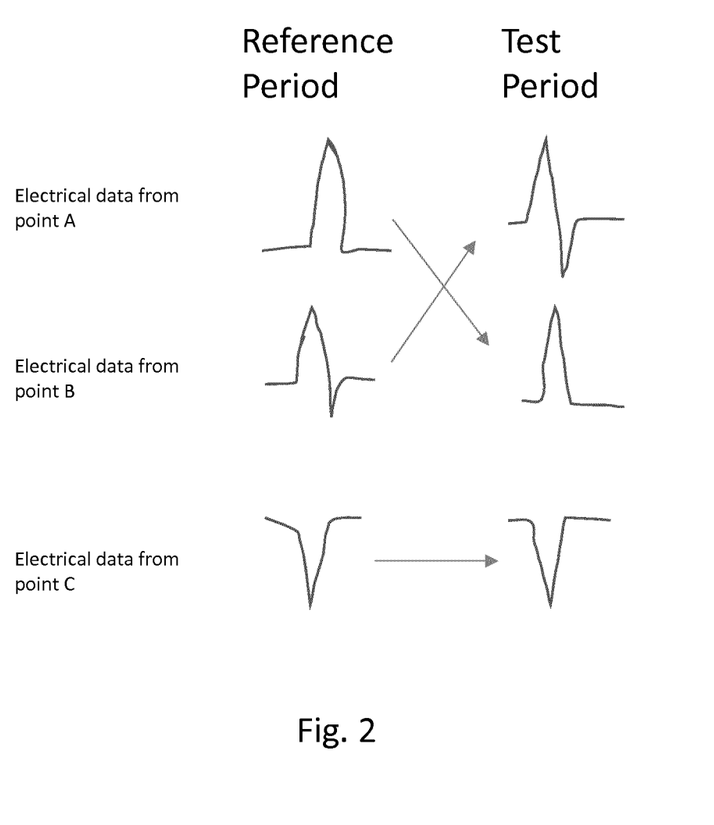
FIG. 2 schematically illustrates a step of matching electrograms.

In Step 5 an index of degree of stimulatory and a time-delay is calculated for every possible pairing of an electrogram in the reference state with an electrogram in the test state. For example this could be the maximal correlation coefficient calculated of the electrical data between the reference and test. Alternative indices of similarity include the Manhattan distance. FIG. 2 schematically illustrates this matching process. In this case, the electrode at point C has not shifted relative to the heart in the test state whereas the electrodes at points A and B have moved such that the electrogram acquired from the electrode at point A in the test state is paired with the electrogram acquired from the electrode at point B in the reference state and vice versa.

Advantageously this would not be calculated as a single correlation coefficient, but a set of similarity indices at different time lags between the reference and test electrogram, with the value to describe the pairing of electrograms being the largest value. The purpose of this is to allow detection of signals that are similar but displaced in time. The reference electrogram that is the most similar to each test electrogram based on the maximal similarity index is selected as the pair for the test electrogram.

Step 6: Advantageously, step 5 could be restricted to not address all combinations of pairings of electrograms, but only those pairs where the positions of the electrograms are likely to be close together.

For example, in one embodiment the electrode data is acquired in association with spatial localisation in relation to each other and/or to landmarks in the body and/or the heart. For example this could be done by imaging modalities exemplified by the CT scan method described in US 20090053102. Alternatively, the electrodes could be carefully placed in pre-specified locations. In another alternative the position of the electrograms could be detected using one of many 3-dimensional spatial localisation tools, such as those described in U.S. Pat. Nos. 6,308,093, 4,649,924 or EP 2627243. For such embodiments, in which each electrogram is associated with spatial localisation data, it is straightforward to calculate the notional distance in 3-dimensional space between any pair of electrograms.

A subset of a list of electrograms to be used for the matching process can be composed by one of many possible algorithms, such as the following:

a) Simply the closest single electrogram.
b) The n closest electrograms, where n is a predefined constant or n is a fraction of the number of electrograms available.
c) All electrograms within a predefined threshold distance or a certain fraction of a function of the size of the heart.
d) Combinations of the above rules.

This process of forming a subset permits step 5 to involve performing relatively fewer similarity index calculations, thereby making the overall computation quicker. It also has the advantage of not forming an inappropriate match between electrograms that are far apart.

Step 7: As the different components (such as the QRS complex, T-wave, or P-wave) of the electrical cardiac cycle may be differentially affected by the test stimuli, in some embodiments steps 4, 5, and 6 can be performed separately on either a single (such as the QRS complex alone), or multiple segments of the electrogram (such as the QRS complex and T-Wave separately). The division of the electrograms into the different segments (with the complete ensemble of electrograms divided as a whole) may either be performed manually by the operator, or using one of several algorithms known to those skilled in the art to identify the approximate points of onset and offset of the segments.

In step 8 each location of the heart is associated with a scalar value representing a relative time-lag to form a map. In one embodiment this map consists of a time delay for each electrode position in the reference phase, comparing it with appropriate corresponding electrogram position in the test phase (which may or may not be the same electrode position, having been selected during steps 5 and optional step 6). In an alternative embodiment, the map consists of the time delay for each test electrode position, comparing it with the reference electrode position.

If the optional step 5 either in combination with or without optional step 6 was carried out, as a by-product, a set of time-lags associated with the maximal similarity are produced for each test electrode. The end result of these steps is a set of pairings between a reference state electrogram and a test state electrogram. For each of these pairings, step 6 provides a signal time lag. The list of all of these time lags for a complete map of the heart (this could be a reference state map, or a test state map) can be composed.

Alternatively, especially if step 5 or step 6 was not carried out, then for each of the pairs of electrodes obtained in step 4 a similarity index (for example, the correlation coefficient, median absolute difference, standard deviation of difference, or Manhattan distance) is generated for every potential time-lag between the two electrograms. The time-lag associated with the maximum similarity is selected as the representative time-lag for that pair of electrograms. This approach can also be used for cases where step 5 (with or without step 6) was carried out.

In either case, another option once the matching electrode pairs have been generated on untransformed data is to repeat the cross-correlation with transformed data (e.g. example f from step 3) for the matched pair (this gives a value that will be more familiar to the fiducial point method that electrophysiologists currently use).

If the optional step 7 was carried out and two or more segments of the electrogram were separately processed (for example the QRS-complex and T-wave segment) then these are combined into a single scalar value by subtraction. For instance, the time-lag associated with the QRS-complex is subtracted from the time-lag associated with the T-wave segment.

Figure 3:
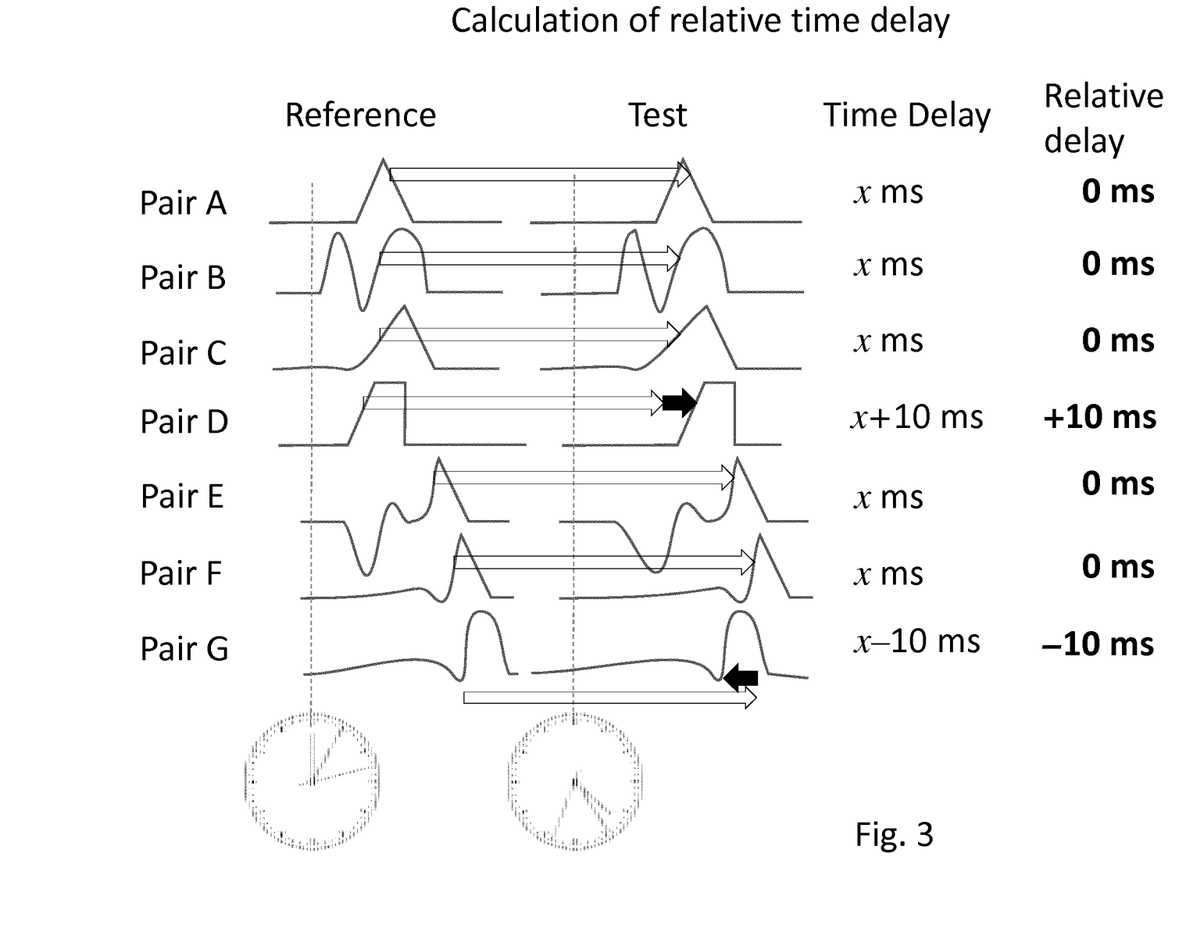
FIG. 3 schematically illustrates a step of calculating a time shift between matched electrograms for a number of spatial locations.

Advantageously, these values are then processed to create smaller numbers suitable for display and interpretation by the following steps. An index of the average of these values is calculated. Advantageously this is the median. Alternatively, this could be the mean or any other measure of central tendency. Typically, all of the time delays for different electrodes will be similar in value to this index value. A new set of values is then calculated by subtracting the index of the average of the values from each of the values in turn. This would be expected to result in a map containing numbers that are centred on zero with some positive and some negative. A positive number does not indicate that events in one electrogram are occurring later than in another electrogram. Rather, it is better understood as indicating that the events in this electrogram are occurring later in the sequence of all events in the test state cardiac cycle than the events in the corresponding electrogram in the reference state cardiac cycle.

This approach is illustrated schematically in FIG. 3. For each pair of matched electrograms (A to G) a time difference in calculated using a clock time. This may, for example, use a clock time associated with the data acquisition system (so long as the same system is used to acquire the reference and test data sets, as would be usual). The median of these delay values is then determined ('x' in the present case) and a relative delay, with respect to this median value, can then be calculated for each pair of electrograms. In this case the relative delay for pair D is +10 ms and for pair G is −10 ms. For all of the other pairs it is zero.

Display of Data

There are many methods available for the display of scalar data as obtained in the steps above when associate with spatial data. Advantageously, the spatial data associated with the electrograms can be display as a series of indications in two-dimensions. A variety of methods are available for converting a 3-dimensional representation to a 2-dimensional representation, and a variety of methods are available for converting the scalar timing data into a visible indication.

One possible method of converting a 3-dimensional representation to a 2-dimensional representation is to convert positions into angular coordinates in relation to a specified point and orthogonal axes, the equivalent of latitude and longitude on a globe; also known as elevation and azimuth, described in the steps below In step 1 a specified point is selected. This might be the centre of the heart which might be calculated from the set of electrode positions by a variety of methods well known to those skilled in the art, including the mean of the coordinates. Alternatively, the operator could select a location.

In step 2 orthogonal axes are obtained. Advantageously, these may be orientated so that they are parallel and orthogonal to significant cardiac structure such as the left anterior descending coronary artery. Advantageously, orientation in respect to the left anterior descending coronary artery segments the heart clearly into a left and right side, with the base of the heart located superiorly, and the apex of the ventricles inferiorly. Orthogonal axes may also be specifically selected by the operator, or in relation to other cardiac or extra cardiac structures.

In step 3, the 3-dimensional location of each electrogram is transformed into two angular co-ordinates that specify the elevation and azimuth in relationship to the orthogonal axes.

In optional step 4 the pairs of angular co-ordinates may be transformed using various projects known to those skilled in the art. These include, the Mercator projection, Gall-Peters projection, Mollweide projection, or any other transform or projection.

In step 5 the angular co-ordinates of the source of the scalar data are graphically displayed on two non-parallel axes with an indication of the scalar value. One appropriate method of converting scalar data to an indication is a colour coded symbol such as a small disc at the appropriate 2-dimensional position described above. For example, blue could represent negative times which means that in the test state, this region has advanced to an earlier point in the sequence of electrical events than the position of this region in the sequence of electrical events in the reference state. In the example, red would represent positive times which would have the opposite meaning. The intensity of the colour could represent the magnitude of the time difference such that, for example, zero time differences are represented as white and progressive more positive times are represented as progressively darker shades of red, whilst progressively negative times are represented by progressively darker shades of blue. The colours described here are intended by way of example and are not intended to be restrictive. Advantageously the visualisation will allow the operator to see the electrogram data associated with each location on the heart.

In optional step 6 the 3-dimensional location of other cardiac structures such as the coronary arteries, valves, or other extra-cardiac structures are transformed using the orthogonal axes obtained in step 2 using the methods of step 3 and 4. Advantageously these structures may then be displayed over or under the representations of the time-lags graphically displayed in step 5. FIG. 4A (discussed further below) shows an example of such a display.

The generated display may be directly interpreted by the operator, assessing the relative electrical spatial-temporal heterogeneity and compared to reference control and pathological cases. Advantageously, a summary of the scalar data over the whole heart or a specific region of interest (for example the right ventricular outflow tract, left ventricle, right ventricle, of left ventricular outflow tract).

Methods to summarise scalar data include:
a) Mean, mode, or median.
b) Standard deviation
c) Range, interquartile range, or other ranges that encompass a specified proportion of values.
d) Mean absolute deviation or median absolute deviation.
e) Or any other method known to those well skilled in the art.

These summary results may be compared to control comparisons (for example a reference and test beat at rest) from the same patient, or to reference values obtained from other control patients (e.g. healthy or diseased patients) to assist a diagnosis.

EXPERIMENTAL EXAMPLE

An ECGi vest was applied to 10 sudden cardiac death (SCD) survivors with no risk factors for SCD prior to index event and controls were 10 patients with concealed Brugada pattern (LR-BrS) and 10 patients undergoing ectopy ablation.

Approximately 500 unipolar reconstructed ventricular EGMs from the ECGi system were used to compare an at-rest beat with a post-exertion beat. Negative differentials were computed for geographically paired EGMs to calculate relative time delay. Normality (N) score was the percentage of ventricle where local activation was <10 ms difference between baseline and test beat. Importantly these can be derived within minutes from the whole dataset without selection bias. Mean N scores were derived for each group at baseline-baseline and baseline-post-exertion and analysed using a one-way ANOVA. It will be appreciated that "baseline" here is an example of the "reference state" discussed above and "post-exertion" is an example of the "test state" discussed above.

FIG. 4A shows a biventricular view with white areas (<10 ms change) or graded red/blue scale of lateness/earliness in a control patient which has minimal change from baseline unlike the SCD survivor. In this image, "LAD" denotes the left anterior descending artery, "MV" denotes the mitral valve and "TV" denotes the tricuspid valve.

Figure 4:
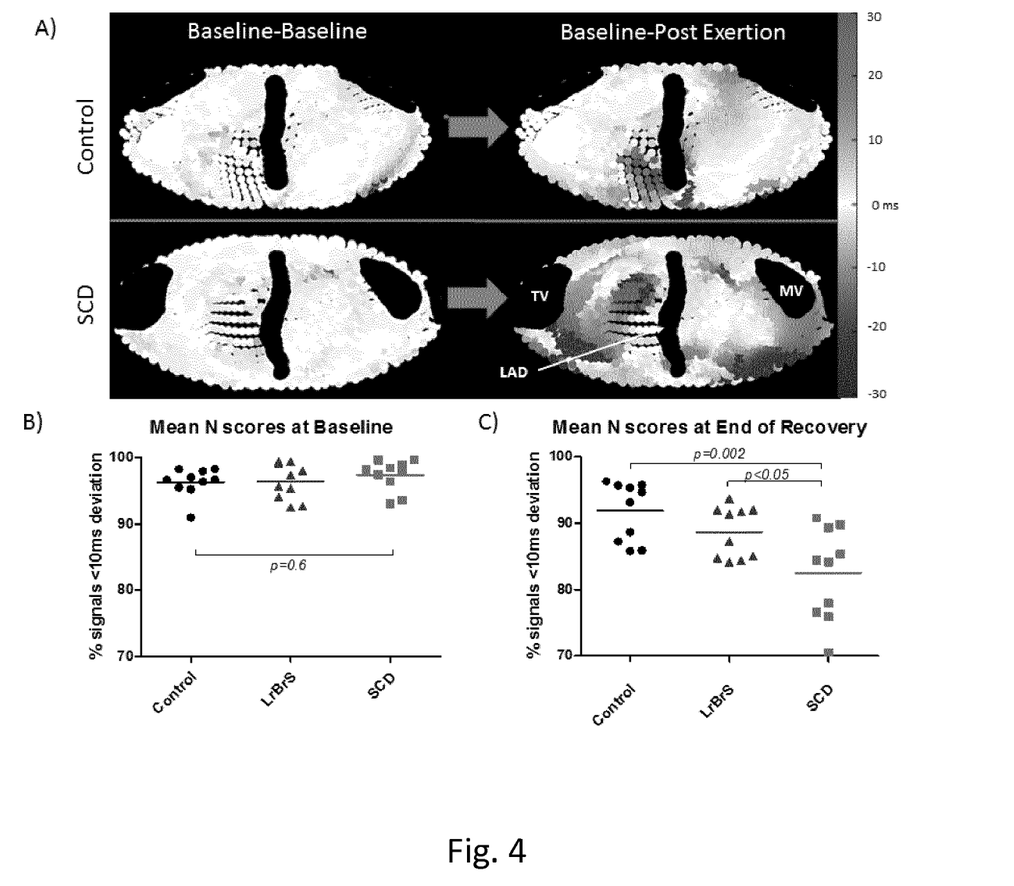
FIG. 4 shows an exemplary graphical display for an output from the analysis for an experimental example.

More specifically, the two display images in the top line of FIG. 4A are for a control patient. The two images in the bottom line of FIG. 4 are for a high-risk patient (i.e. a patient at risk of sudden cardiac death—in this particular example a SCD survivor). For each line, the left-hand images show the 2D map output of relative time delays between two time points that are both in a rest state (5 mins apart in this example). As expected, there is no appreciable relative delay between the two time points for any spatial locations. The two images in the right-hand column, on the other hand, show the results of a comparison of data between a rest state and a stimulated state (immediately following exercise). It can be seen that for the control patient there is very little appreciable relative delay between the two time points for any spatial locations. However, for the at-risk patient the blue and red regions on the map indicate significant relative delays (negative and positive delays respectively) in some spatial locations.

FIGS. 4B and 4C show mean N scores for the three groups tested at Baseline (i.e. "reference state") and at End of Recovery (i.e. "test state"). At rest all three groups had similar mean N scores (SCD: 97% vs LrBrS: 96% vs Control: 96%, p=ns). At post exertion the SCD group had the lowest N score followed by LrBrS and then controls (82% 89% vs 92%, p=0.002). Post-hoc analysis also confirmed a difference between the SCD and LrBrS group at end of recovery (82% vs 89%, p<0.05).

Thus, it can be seen that an approach in line with embodiments of the present invention can be used to identify 'real-time' beat-to-beat variations in global activation timing and the example here demonstrates pro-arrhythmic substrate during exercise in SCD survivors.

The invention claimed is:

1. A method of determining risk-stratification of cardiac conditions, the method comprising:
using a reference data set of electrophysiological data captured from a patient in a reference state and at least one test data set of electrophysiological data captured from the patient in a test state, each data set defining a plurality of electrograms at a given point in time for a respective plurality of spatial locations relative to a heart of the patient;
processing the electrophysiological data by:
matching each electrogram in the reference data set to a corresponding electrogram in the at least one test data set to create a pair of matched electrograms between two time-points for each of the plurality of spatial locations; and
for each spatial location of the plurality of spatial locations:
deriving a relative time delay for the spatial location by calculating a time displacement of waveforms between the electrograms of the pair of matched electrograms between the two time-points for that spatial location, wherein the relative time delay is determined based on one or more correlation values calculated at each of a set of time delays between the electrograms of the pair of matched electrograms between the two time-points for the spatial location; and
determining a confidence value associated with the relative time delay for the spatial location; and
generating, based on the relative time delays and the confidence values determined for the plurality of spatial locations, an output that represents a summary of the time displacements of the waveforms over the whole heart to directly determine a real-time beat-to-beat variation in global activation timing between the two time-points.

2. The method according to claim 1, wherein the reference state is a rest state.

3. The method according to claim 1, wherein the test state is a post-stimuli state following application of a physiological or pharmacological stimulus to the patient.

4. The method according to claim 1, wherein the spatial locations are locations on an internal or external surface of the heart.

5. The method according to claim 1, further comprising generating an output that comprises the spatial locations and associated time delays.

6. The method according to claim 5, further comprising displaying the output to a user, wherein displaying the output to a user comprises representing the spatial locations in a two-dimensional map and indicating relative magnitudes of the time delays associated with the spatial locations at a respective position on the two-dimensional map.

7. The method according to claim 6, further comprising indicating on the two-dimensional map a location of one or more cardiac structures.

8. The method according to claim 4, further comprising comparing the output with a control output to provide a measure of a susceptibility of the patient's heart to developing arrhythmias.

9. The method according to claim 1, further comprising a data acquisition step prior to said processing of the electrophysiological data, the data acquisition step comprising acquiring the reference data set of electrophysiological data from the patient, changing a stimulus state of the patient, and then acquiring the at least one test data set of electrophysiological data from the patient.

10. The method according to claim 1, wherein each electrogram is directly measured by an electrode disposed on an internal or external surface of the heart, the spatial locations being locations of the electrodes, and the step of matching an electrogram in the reference data set to a corresponding electrogram in the at least one test data set comprises matching electrograms measured by the same electrode.

11. The method according to claim 1, wherein each electrogram is calculated from signals taken from one or more electrodes on skin of the patient, the spatial locations being locations on a surface of the heart, and the step of matching an electrogram in the reference data set to a corresponding electrogram in the at least one test data set comprises matching electrograms calculated using signals from the same electrode or electrodes.

12. The method according to claim 1, wherein the step of matching an electrogram in the reference data set to a corresponding electrogram in the at least one test data set comprises calculating a degree of similarity between the electrogram from the reference data set and each of a plurality of electrograms from the at least one test data set, the electrogram from the at least one test data set with the highest degree of similarity being selected as the corresponding electrogram to match to the electrogram from the reference data set.

13. The method according to claim 12, wherein for each electrogram in the reference data set a degree of similarity is calculated only for a subset of the electrograms in the at least one test data set.

14. The method according to claim 13, wherein the subset of the electrograms in the at least one test data set are selected based on their spatial proximity to the electrogram in the reference data set with respect to which the degree of similarity is being calculated and wherein the electrophysiological data captured from the patient using electrodes and is captured with associated spatial data defining locations of the electrodes relative to one another and/or relative to anatomical landmarks, this associated spatial data being used to determine the spatial proximity of the electrograms.

15. The method according to claim 1, wherein calculating each of the set of the time delay between the electrograms comprises dividing each electrogram into two or more segments and calculating the time delay between one or more corresponding segments of the matched electrograms.

16. The method according to claim 1, wherein the electrophysiological data comprises multiple electrograms for each spatial location, the relative time delay being derived by matching multiple electrograms in the reference data set to a corresponding number of electrograms in the at least one test data set to create multiple matched pairs of electrograms for each of the plurality of spatial locations from which the relative time delay is derived.

17. The method according to claim 16, wherein for each spatial location the set of time delays between the multiple matched pairs of electrograms are averaged to determine the relative time delay for that spatial location.

18. The method according to claim 1, wherein the electrophysiological data is captured from the patient using more than 10 electrodes.

19. The method according to claim 1, wherein each data set of electrophysiological data comprises at least 50 electrograms.

20. An apparatus for determining risk-stratification of cardiac conditions, the apparatus comprising:

a memory storing a reference data set of electrophysiological data captured from a patient in a reference state and at least one test data set of electrophysiological data captured from the patient in a test state, each data set defining a plurality of electrograms at a given point in time for a respective plurality of spatial locations relative to a heart of the patient; and a processor configured to access data in the memory and is operable to:
    match each electrogram in the reference data set to a corresponding electrogram in the at least one test data set to create a pair of matched electrograms between two time-points for each of the plurality of spatial locations;
    for each spatial location of the plurality of spatial locations:
        derive a relative time delay for the spatial location by calculating a time displacement of waveforms between the electrograms of the pair of matched electrograms between the two time-points for that spatial location, wherein the relative time delay is determined based on one or more correlation values calculated each of a set of time delays between the electrograms of the pair of matched electrograms between the two time-points for the spatial location; and
        determine a confidence value associated with the relative time delay for the spatial location; and
    generate, based on the relative time delays and the confidence values determined for the plurality of spatial locations, an output that represents a summary of the time displacements of the waveforms over the whole heart to directly determine a real-time beat-to-beat variation in global activation timing between the two time-points.

\* \* \* \* \*